United States Patent
Margus et al.

(10) Patent No.: US 7,135,286 B2
(45) Date of Patent: Nov. 14, 2006

(54) PHARMACEUTICAL AND DIAGNOSTIC BUSINESS SYSTEMS AND METHODS

(75) Inventors: Bradley A. Margus, Boca Raton, FL (US); David R. Cox, Belmont, CA (US); Stephen P. A. Fodor, Palo Alto, CA (US)

(73) Assignee: Perlegen Sciences, Inc., Mountain View, CA (US)

( * ) Notice: Subject to any disclaimer, the term of this patent is extended or adjusted under 35 U.S.C. 154(b) by 458 days.

(21) Appl. No.: 10/107,508

(22) Filed: Mar. 26, 2002

(65) Prior Publication Data

US 2003/0186244 A1 Oct. 2, 2003

(51) Int. Cl.
*C12Q 1/68* (2006.01)
(52) U.S. Cl. .............................. 435/6; 702/20
(58) Field of Classification Search .................... 435/6; 702/19, 20; 705/500
See application file for complete search history.

(56) References Cited

U.S. PATENT DOCUMENTS

| 5,525,464 | A | * | 6/1996 | Drmanac et al. ............. 435/6 |
| 5,972,614 | A | | 10/1999 | Ruano et al. .................. 435/6 |

FOREIGN PATENT DOCUMENTS

| WO | WO 01/01218 A2 | 1/2001 |
| WO | WO 01/04270 A1 | 1/2001 |
| WO | 0180156 | 10/2001 |

OTHER PUBLICATIONS

Jones, Electronic Journal of Biotechnology 3 (2), Aug. 15, 2000.*
Roses, Lancet 355: 1358 (Apr. 15, 2000).*
Goddard et al, Am. J. Hum. Genet. 66: 216 (2000).*
Form 10-K filed by Millennium Pharmaceuticals, for the fiscal year ended Dec. 31, 2000.
Form 10-K filed by Applera Corporation, for the fiscal year ended Jun. 30, 2001.
Form 10-K filed by Genzyme Corporation, for the fiscal year ended Dec. 31, 2000.
Form 10-K filed by Human Genome Sciences, Inc., for the fiscal year ended Dec. 31, 2000.
Form 10-K filed by Genaissance Pharmaceuticals, for the fiscal year ended Dec. 31, 2000.
Perlegen Sciences, Inc. Private Placement Memorandum, dated Mar. 30, 2001.
San Jose Mercury News article entitled "Gene Hunters" dated Jan. 21, 2002.
Patil, N., Cox, D.R. et al "Blocks of Limited Haplotype Diversity Revealed by High-Resolution Scanning of Human Chromosome 21" *Science Magazine* 294, 1719-1723 (2001).
Daly, M.J., Lander, E.S., et al. "High-resolution haplotype structure in the human genome" *Nature Genetics* 29, 229-232 (2001).
Oestreicher, P., "4th Annual Pharmacogenomics and Medicine Lectures" *Pharmacogenomics* 2 (3), 291-296 (2001).

* cited by examiner

*Primary Examiner*—James Martinell
(74) *Attorney, Agent, or Firm*—Deana A. Arnold; Gulshan H. Shaver, Esq.

(57) ABSTRACT

Improved pharmaceutical and diagnostic business systems and methods are disclosed. One or more genomes are scanned for single nucleotide polymorphisms. The polymorphisms are assigned to haplotype blocks, and representative SNPs from the haplotype blocks are used in association studies for pharmaceutical and diagnostic development.

8 Claims, 1 Drawing Sheet

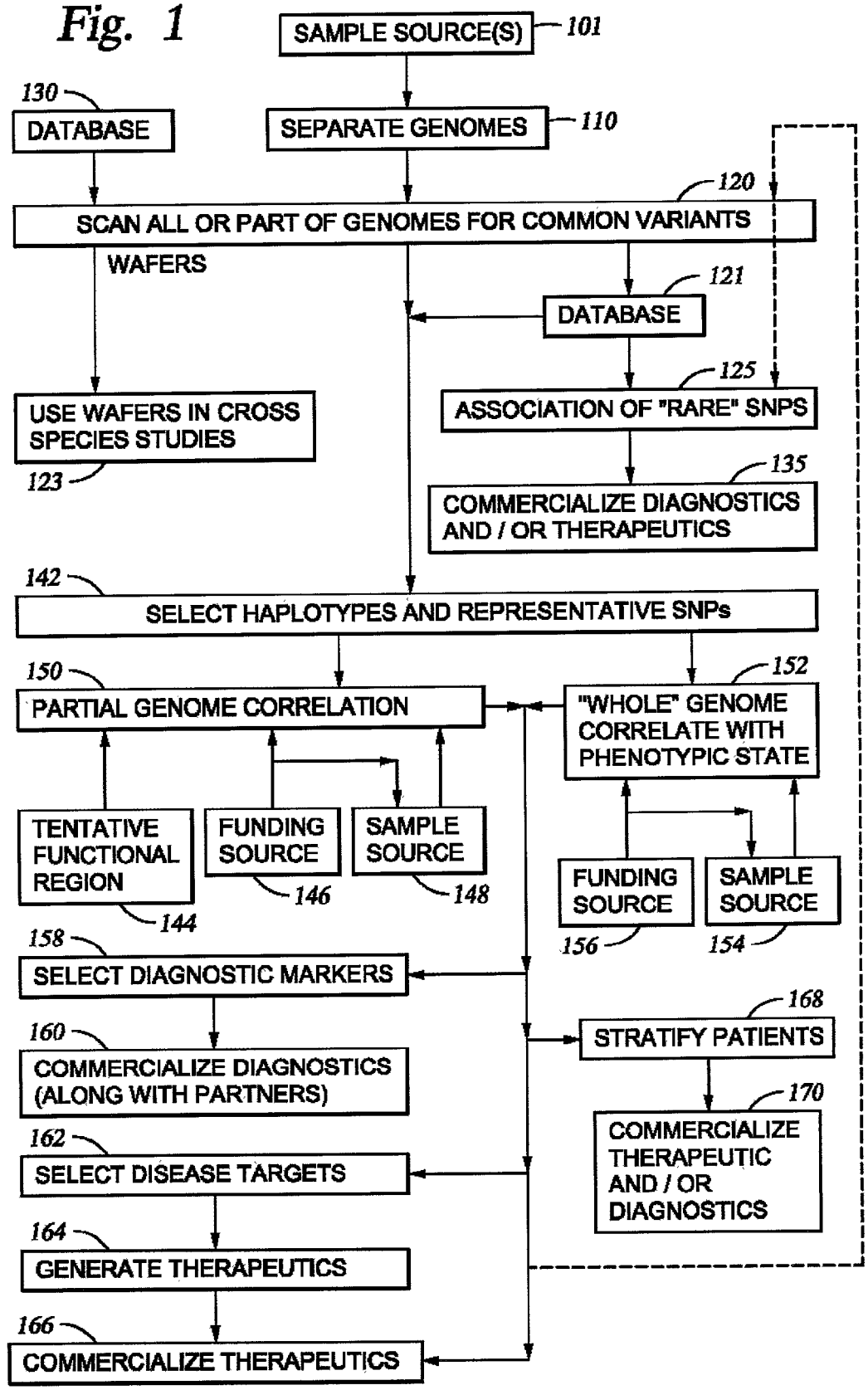

PHARMACEUTICAL AND DIAGNOSTIC BUSINESS SYSTEMS AND METHODS

BACKGROUND OF THE INVENTION

The DNA that makes up human chromosomes provides the instructions that direct the production of all proteins in the body. These proteins carry out the vital functions of life. Variations in DNA often produce variations in the proteins or changes in expression of protein, thus affecting the function of cells. Although environment often plays a significant role, variations or mutations in DNA are directly related to almost all human diseases, including infectious diseases, cancers, inherited disorders, and autoimmune disorders. Moreover, knowledge of human genetics has led to the realization that many diseases result from either complex interactions of several genes or from any number of mutations within one gene. For example, Type I and II diabetes have been linked to multiple genes, each with its own pattern of mutations. In contrast, cystic fibrosis can be caused by any one of over 300 different mutations in a single gene.

Additionally, knowledge of human genetics has led to a limited understanding of differences between individuals when it comes to drug response—the field of pharmacogenetics. Since the first correlation over half a century ago of adverse drug responses with amino acid variations in two drug-metabolizing enzymes, plasma cholinesterase and glucose-6-phosphate dehydrogenase, careful genetic analyses have linked sequence polymorphisms in drug metabolism enzymes, drug targets and drug transporters with compromised levels of drug efficacy or safety. In the clinic, such information is being used to prevent drug toxicities; for example, patients are often screened for genetic differences in the thiopurine methyltransferase gene that cause decreased metabolism of 6-mercaptopurine or azathiopurine. Yet only a small percentage of observed drug toxicities have been explained adequately by the set of pharmacogenetic markers validated to date. In addition, insufficient therapeutic efficacy or unanticipated side effects in "outlier" individuals when administered drugs previously demonstrated to be both safe and efficacious in clinical trials is a tremendous problem for health care practitioners and presents a significant dilemma to the pharmaceutical industry.

Disease-related and pharmacogenetic gene validation relies on elements of population and quantitative genetics and robust statistical metrics; however, the first step normally relies upon identification of a candidate target gene. To date, various biotechnological methods have been employed to identify candidate genes. For example, differential gene expression has been employed, essentially looking for differences in gene expression between affected and unaffected individuals or between treated and untreated individuals. In addition, protein-protein interaction maps to identify drug receptors and their immediate effectors have been used. Another approach involves mining human sequence databases for sequences similar to accepted disease-related or pharmacokinetic or pharmacodynamic regulators.

Because any two humans are 99.9% similar in their genetic makeup, most of the sequence of the DNA of their genomes is identical. However, there are variations in DNA sequence between individuals. For example, there are deletions of many-base stretches of DNA, insertion of stretches of DNA, variations in the number of repetitive DNA elements in noncoding regions, and changes in single nitrogenous base positions in the genome called "single nucleotide polymorphisms" or "SNPs". It is estimated that there are 3 to 4 million common SNPs that occur in at least 10 percent of people. These common SNPs do not occur independently but are passed from generation to generation in variable-length blocks of multiple SNPs, forming patterns across the genome. Such blocks of SNPs are called SNP haplotype blocks herein.

The candidate gene identification strategy most relevant to SNPs is whole-genome association of various populations of individuals—that is, scanning the entire genomes of populations of individuals to correlate SNPs to disease or drug response. Such whole-genome analyses would provide a fine degree of genetic mapping and pinpoint specific regions of linkage. Methods have been proposed and are used in connection with whole genome analysis. For example, the methods described in U.S. Ser. No. 60/327,006, filed Oct. 5, 2001, "Identifying Human SNP Haplotypes, Informative SNPs and Uses Thereof," assigned to the assignee of the present invention (incorporated herein by reference for all purposes) have been proposed for use in such applications. U.S. Ser. No. 10/166,341, filed Sep. 18, 2001, "Human Genomic Polymorphisms", assigned to the assignee of the present invention incorporated herein by reference for all purposes, provides the identity of SNPs and SNP haplotype blocks across one representative chromosome, ie. Chromosome 21.

It is desirable to establish new and useful business methods to capitalize on the understanding of genetics.

SUMMARY OF THE INVENTION

Improved business methods, devices, and systems for utilizing genetic information are provided.

According to one embodiment of the invention a business method is provided that includes the steps of scanning the human genome for single nucleotide polymorphisms across more than 10,000,000 bases, including both genic and non-genic regions; grouping said single nucleotide polymorphisms into haplotype blocks; and independently or collaboratively with drug companies using said haplotype blocks in association studies with disease states. According to another embodiment of the invention a business method is provided that includes the steps of scanning the human genome for common single nucleotide polymorphisms across more than 10,000,000 bases; grouping said common single nucleotide polymorphisms into haplotype blocks; and collaboratively with drug companies, using the haplotype blocks in association studies with disease states.

BRIEF DESCRIPTION OF THE DRAWINGS

FIG. 1 is a flow chart illustrating aspects of the business method herein.

DETAILED DESCRIPTION OF THE PREFERRED EMBODIMENTS

As used in the specification, "a" or "an" means one or more. As used in the claim(s), when used in conjunction with the word "comprising", the words "a" or "an" mean one or more. As used herein, "another" means at least a second or more. Reference now will be made in detail to various embodiments and particular applications of the invention. While the invention will be described in conjunction with the various embodiments and applications, it will be understood that such embodiments and applications are not intended to limit the invention. On the contrary, the invention is intended to cover alternatives, modifications and equivalents that may be included within the spirit and scope of the invention. In addition, throughout this disclosure various patents, patent applications, websites and publications are referenced. Unless otherwise indicated, each is incorporated by reference in its entirety for all purposes. Processes that may be used in specific embodiments of the methods herein are described in more detail in the following patent applications, all of which are specifically incorporated herein by reference: U.S. provisional patent application Ser. No. 60/280,530, filed Mar. 30, 2001; U.S. provisional patent application Ser. No. 60/313,264 filed Aug. 17, 2001; U.S. provisional patent application Ser. No. 60/327,006, filed Oct. 5, 2001, all entitled "Identifying Human SNP Haplotypes, Informative SNPs and Uses Thereof"; provisional patent application Ser. No. 60/332,550, filed Nov. 26, 2001, entitled "Methods for Genomic Analysis"; U.S. Pat. No. 6,969,589, entitled "Methods for Genomic Analysis"; and U.S. Pat. No. 6,897,025, entitled "Genetic Analysis Systems and Methods"; the disclosures all of which are specifically incorporated herein by reference.

I. General.

Scientists have completed the first draft of the genetic sequence of a human being, marking the beginning of a new era in biological research. Although this in itself is a significant event for mankind, the greater value will be created by reading and comparing the entire DNA sequence of many individuals and finding meaning in the patterns of variation between them.

Everyone's DNA is pretty much the same. Any two humans share 99.9 percent the same DNA sequence. All humans have the same 100,000 or so genes, which are organized into 23 chromosomes. But "pretty much the same" is not exactly the same. There are differences in DNA—about 0.1 percent, or one letter out of every 1,000 is different. Therefore, there are currently estimated to be roughly 3 to 4 million common differences between individuals, and many more rare differences. These differences are responsible for all the inherited aspects of the variations among people, from eye color to height to health.

Most common diseases have a genetic basis, often the result of numerous genetic factors rather than just one gene. Therefore, when scientists want to understand the genetic causes and resulting biological pathways involved in disorders like Alzheimer's, cancer or asthma, they need to compare the DNA variations of the entire genome of many individuals who have the disease to the genomes of many people who do not have the disease.

Similarly, if a drug company has invested hundreds of millions of dollars to develop a new product, only to find that some clinical trial participants have unacceptable side-effects (or do not respond to a drug), that company must be able to predict which individuals in the population will and will not tolerate the drug, or will and will not see an impact from the drug. To associate genetic profiles to drug tolerance, the company needs to scan the genetic profiles of many of the participants in the trial and identify the genetic basis of intolerance. Only then can it obtain regulatory approval to market the drug and to recoup its research and development investment.

By scanning an initial set of genomes, the present method identifies the common patterns or "haplotypes" in which genetic variations or "SNPs" occur. Once these haplotypes are known, assays are used to determine the genetic profiles of many individuals by reading only a few SNPs from each known block of SNPs. This information can be used directly in drug discovery and in discovery efforts with partners.

As a result, the present business method will have a tremendous advantage in conducting genetic association studies for pharmaceutical partners, because it will identify blocks of variation and specific variations across the genome. In some cases, instead of reading all 3 billion bases from each genome, or even the 3 to 4 million common SNPs that may be found, it may be possible to read 300,000 to 500,000 SNPs or less, yet make potential associations against up to all of the genome of an organism. The haplotype patterns seen by reading these particular SNPs provides enough information to allow statistically accurate association data to be extracted from specific populations. Pharmaceutical partners, for example, may then pay to associate genetic profiles with disease symptoms, drug responses, or other phenotypic states.

With initial funding from partners and others, the present method provides for a comparison of human DNA with the DNA of various animals in order to identify non-gene regions of DNA that are conserved between species through evolution. Scientists involved in drug discovery believe these regions may contain long sought-after instructions that regulate important genes.

II. Scientific Basis.

The human body contains about 100 trillion cells. Inside each cell is a center called a nucleus. Inside the nucleus are two complete sets of human chromosomes which contain genetic material. One set of chromosomes is inherited from the mother and one comes from the father. Each set includes the similar genetic information on the same twenty-three chromosomes.

In practice, however, there are small and subtle differences between the paternal and maternal versions of each genome. In fact, except for identical twins, every individual's genome has millions of subtle differences from every other individual's genome. The subtle differences between the genetic material of individuals is what accounts for most differences between people, such as eye and skin color. In addition, genetic variability determines an individual's predisposition to disease, response to drugs, reaction to the environment, and even in some cases, behavior.

The human genome is gigantic. It is often compared to a book written in a four-letter alphabet using a total of three billion letters, or about one billion words. This makes one person's genome as long as 800 Bibles. If one were to read the genome out loud at the rate of one word per second on 8 hours shifts, it would take about century. It is an immense document, yet it fits inside the microscopic nucleus of a tiny cell that fits easily upon the point of a pin.

Just like a book, the human genome is a piece of "digital" information written in linear, one-dimensional form and defined by a code that transliterates a small alphabet into a large lexicon of meanings through the order of their groupings. Whereas English books are written in words of variable length using twenty-six letters, genomes are written primarily in three-letter words, using only four letters: A, C, G and T (which stand for adenine, cytosine, guanine and thymine). And instead of being written on flat pages, they are written in long chains of sugars and phosphates called DNA molecules (for deoxyribonucleic acid) to which the letters or "bases" are attached as side rings. Each chromosome is one double helix of very long DNA molecules.

An individual's genomic DNA affects numerous facets of life by providing, for example, the instructions that direct the production of all proteins in the body. These proteins carry out the vital functions of life. Misspellings or "mutations" in DNA produce mistakes in the proteins that are produced by cells, thus affecting the normal function of the cells, or in regulatory elements of the cells. Although the environment often plays a significant role, variations or mutations in DNA are directly related to almost all human diseases, including infectious diseases, cancers, inherited disorders, and autoimmune disorders. Being able to compare the DNA of many individuals and associating those variations to clinical symptoms provides a powerful tool for understanding, diagnosis and treatment of a disease.

Knowledge of human genetics has led to the realization that many diseases result from either complex interactions of several genes and their products or from any number of mutations within one gene. For example, Type I and II diabetes have been linked to multiple genes, each with its own pattern of mutations.

The complexity of the genetic basis of disease highlights the need for new technology capable of looking across the entire genome to analyze large numbers of variations. Business methods based upon scanning entire genomes is an aspect of the invention herein.

To implement the methods herein, one aspect of the invention provides for the separation of the full sets of chromosomes from individuals (such as more than 10, preferably more than 20, more preferably more than 25 and more preferably more than 50 individual genomes) so that there are multiple unique genomes. Preferably, haploid genomes or portions thereof are used, by using the methods described in U.S. Ser. No. 60/332,350, filed Nov. 26, 2001. The bases of all or a significant part of these genomes are then scanned or sequenced using, for example, conventional DNA sequencers or chip-based technologies. In a preferred embodiment, whole-wafer technology from Affymetrix, Inc. of Santa Clara, Calif. is used to read each of the genomes at single-base resolution. DNA sequence data generated from each genome may then be compared with the other genomes in order to discover all or many of the variations among the genomes. For example, individual 2 in Table 1 below has two variations as compared with individuals 1 and 3:

TABLE 1

| Individual 1: | T | A | G | T | C | G |
|---|---|---|---|---|---|---|
| Individual 2: | T | A | A | T | C | C |
| Individual 3: | T | A | G | T | C | G |

Because all humans are 99.9% similar in their genetic makeup, most of the letters of their genomes will be identical. One would expect to discover about 3 to 4 million common variations between 50 scanned genomes with "common" variations, defined in some cases as those variations that occur in at least 10 percent of people. Most single nucleotide polymorphisms or "SNPs" do not occur independently but are passed from generation to generation in variable-length blocks of multiple SNPs, forming patterns across the genome that form an individual's genetic profile. These patterns are referred to as "haplotypes". In scanning the first, for example 20 to 50 genomes, it will be possible to identify common haplotypes in which SNPs occur. After identifying these haplotypes it becomes possible to determine the sequence of individuals by reading only a few SNPs from each known block of SNPs. This approach has a tremendous advantage in conducting genetic association studies for pharmaceutical partners, because it utilizes a reduced set of specific SNPs that are indicators for the state of the entire genome. Instead of reading all 3 billion bases from each genome, or even the 3 to 4 million common SNPs that may be found, one may read, for example, only 300,000 to 500,000 informative SNPs, once they are discovered. The haplotype patterns seen by reading these particular SNPs allows statistically accurate association data to be extracted from specific clinical populations.

According to one aspect of the invention, glass wafers on which high density arrays of DNA probes (short segments of DNA) have been placed are used. Each of these wafers holds, for example, approximately 60 million DNA probes that can be used to recognize longer sample DNA sequences. The recognition of sample DNA by the set of DNA probes on the glass wafer takes place through the mechanism of DNA hybridization. When a DNA sample hybridizes with an array of DNA probes, the sample will bind to those probes that are complementary to sample DNA sequence. By evaluating to which probes the sample DNA hybridizes more strongly, it is possible to determine whether a known sequence of DNA is present or not in the sample DNA.

The use of DNA probe arrays to decipher genetic information involves the following steps: design and manufacture of DNA probe array wafers, preparation of the sample, hybridization of target DNA to the array, detection of hybridization events and data analysis to determine sequence. The preferred wafers are manufactured using a process adapted from semiconductor manufacturing to achieve cost effectiveness and high quality, as from Affymetrix, Inc.

Once fabricated, DNA probe arrays can be used to decipher genetic information. A DNA sample is isolated, amplified, and tagged with a fluorescent reporter group by standard biochemical methods. The labeled sample is incubated with a wafer, and segments of the sample bind, or hybridize, with complementary sequences on the wafer. The wafer is then scanned and the patterns of hybridization are detected by emission of light from the fluorescent reporter groups. Because the identity and position of each probe on the wafer is known, the identity of the DNA sequence applied to the wafer can be determined. In the case where variations are found, decreased hybridization is observed.

The design of the wafers begins by probe selection. The probe selection algorithms are based on ability to hybridize to the particular DNA sequence to be scanned. With this information, computer algorithms are used to design photolithographic masks for use in manufacturing the probe arrays.

Probe arrays are manufactured by light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. This parallel process enhances reproducibility and helps achieve economies of scale.

Once fabricated the arrays are ready for hybridization. The nucleic acid to be analyzed (the target) is isolated, amplified and labeled with a fluorescent reporter group. The labeled target is then incubated with the array using a fluidics station and hybridization oven. After the hybridization reaction is complete, the array is inserted into the scanner, where patterns of hybridization are detected. The hybridization data are collected as light emitted from the fluorescent reporter groups already incorporated into the target, which is now bound to the probe array. Probes that most clearly match the target produce stronger signals than those that have mismatches. Since the sequence and position of each probe on the array are known, by complementarity, the identity of the target nucleic acid applied to the probe array can be identified.

Because of the public availability of raw human genome sequence data and the ongoing demand from pharmaceutical companies for information useful in developing new drugs and improving the efficacy of existing drugs, it is possible to institute a business based on information from this technology. The technology allows for improved effectiveness and efficiency of research and development to develop new, more effective medicines, the launching of which is a key to pharmaceutical company profits.

III. Business Applications

The research and development process from discovery to launch is currently lengthy, expensive and risky. On average, it takes fourteen years to develop a product from the research laboratory to FDA approval. Any event that delays the commercial development process can cost the affected company a loss of revenue up to $1 billion annually. Conversely, any change to the process that might accelerate the development cycle brings significant potential financial benefit to the companies that implement such changes.

Accelerated time-to-market not only brings the benefit of earlier sales revenues but the expanded market share enjoyed by companies that are the first to enter a segment before its competitors. This is critical, because the period of market exclusivity for the first drug in a new market therapeutic class is typically much shorter than would be desirable. Consequently, marketing expenditures have increased rapidly as companies attempt to maintain or increase market share.

In addition to the time-to-market factors, the odds of any compound successfully making it through all of the steps across fourteen years are miniscule: out of 5,000 compounds that begin in pre-clinical development, only five make it to clinical trials, and only one of those is likely to reach the market. The combination of long development cycles and high failure rates results in an average cost of approximately $500 million per successful compound.

Pharmaceutical companies have recognized the need to improve research and development efficiency by utilizing genomics in their drug discovery programs. This effort is necessary for companies to match historical revenue growth levels and to meet shareholders' expectations. The drive by pharmaceutical companies for efficiency provides an opportunity for application of genome-wide scanning technologies during both the research and clinical development cycle.

One example of the application of the business herein can be found in population segmentation. It is generally acknowledged that most drugs work more effectively for some patients than others. Because this variability in patient response is often poorly understood, pharmaceutical companies may unnecessarily discontinue further drug development, fail to obtain regulatory approvals for promising drug candidates, or, even if approvals are obtained, be unable to market an approved drug effectively or to obtain approval for third party reimbursement.

Genomic differences have long been recognized as influencing how patients respond to drugs. However, pharmaceutical companies generally have not considered genomic differences between patients in developing and implementing clinical trials or in the marketing of approved drugs. By correlating genomic variation with drug response in clinical trials, it is possible to improve the drug development and marketing process. For example, pharmaceutical companies could use the correlation data from phase I and phase II clinical trials to make better informed decisions on whether or not to enter phase III clinical trials. In addition, understanding the correlation between genomic differences and drug response would enable pharmaceutical companies to improve the marketing of their drugs by identifying those patients for whom particular drugs are likely to be more effective. By use of the information herein a company may be able to market a drug by segregating a responder population from a non-responder population, or be segregating a population that encounters negative effects from a drug from a population that does not suffer a negative (or even toxic) response.

Drugs are typically developed to interact with a single version of a given protein or receptor in the human body. A drug may therefore, for example, only be effective in individuals that carry the specific protein or receptor for which the drug was designed. Individuals who have a genetically-caused variation in these proteins or receptors, or the proteins involved in the metabolism of the drug, may not respond to the drug or may experience adverse side effects.

The methods used by the pharmaceutical industry to develop new drugs and to improve existing drugs may be changed when genetic variation is taken into account. Genetic variation may play a significant role in all stages of drug discovery and development. Genetic variation information can also be used to improve drugs already on the market by providing information to select the best drug for a particular patient.

As genetic variation becomes better understood at the molecular or genomic level, it is clear that an individual's response to a drug is dependent upon that individual's unique genome. In addition, more than one gene generally determines how an individual responds to a drug. Every drug generally interacts, directly and indirectly, with a variety of different proteins produced by different genes. Therefore, in order to predict a specific drug response, genomic variation in multiple genes must be analyzed.

A practical approach to understanding why individuals have different responses to the same drug is found in grouping individuals together based upon specific genomic similarity. This genomic similarity can occur in unrelated individuals from different geographic regions.

This ability to identify and associate genetic variations with disease and drug responses across the entire genome will facilitate the entire drug development process and may reduce the time-to-market for therapeutics. Genetic profiles on selected subsets of patient populations may be used to enable pharmaceutical companies to identify drug targets, to focus on potentially better leads earlier in preclinical stage studies, and to move more quickly into screening assays. In addition, better targets may identify opportunities for safer, more effective points of therapeutic intervention.

Markets that may be addressed by the process herein includes not only evaluation of genetic variation and drug response, but also genetic variation to determine and validate targets, evaluation of variation and disease risk, identification of conserved non-coding regions that may contain gene regulatory sequences, the study of genetic variation in regulatory regions affecting development, and other geneotype-phenotype associations with commercial potential, such as in consumer products. Potential customers for genome-wide pattern information, conserved region information, patient profiling services and other scientific partnerships include numerous companies in the pharmaceutical and biotechnology industries. In addition, through a better understanding of the basis of disease, other methods of drug discovery will be facilitated.

Information generated by whole-genome variation scanning of multiple individuals will be highly valued by pharmaceutical drug discovery programs that require a clearer understanding of genetic influences on disease and drug response. Genome-wide analysis of variations between patient groups will not only reduce the costs and time-to-market for new therapeutics but may also elucidate why individuals respond differently to their environments and to treatments.

The business strategy herein includes further developing, for example, DNA-scanning and wafer technology and using that technology's genome scanning capability to identify commercially valuable genetic associations through research collaborations. Up-front fees, research payments, milestone payments, database subscriptions and royalties may all contribute revenue to the business model.

In the short-term, the business strategy may generate revenues in two main areas. First, revenue may be obtained by providing genomic data obtained and analyzed from reading and genotyping haplotypes from multiple individuals to biotech and pharmaceutical partners on a non-exclusive basis. In addition or alternatively, one may enter into discovery contracts on an exclusive or non-exclusive basis with pharmaceutical companies that are interested in specific areas of the genome, or specific disease areas across large portions or all of the genome, even before scanning the first genomes. In addition, the methods herein may be used to verify (or remove as candidates) existing drug target candidates.

In the mid-term, four areas may add or replace other sources of revenue. First, one may enter into collaborative agreements to provide genome-wide sequencing and genetic profiling (association studies) services that enable biotech, pharmaceutical and agricultural partners to analyze specific populations. These populations may be groups affected by a particular disease, participants in clinical trials, or groups displaying some other phenotype such as a particular response to a drug or environmental stimulus. Second, contract and grant funding from non-profit, grant-giving organizations such as the federal government may be used in either haplotype discovery or association studies. Further, pharmaceutical partners would contract for research funded by those pharmaceutical partners. Still further, as part of an inter-company cross-licensing agreement, chip or other platform suppliers will pay a royalty on sales to its customers of chips or other technologies containing content generated by the business.

Longer term, revenues may also be generated by royalties on products developed and commercialized by partners using the haplotype data or even direct sales of drugs. The identification of associations between groups of variations and clinical symptoms will be extremely valuable in identifying drug targets as well as optimizing existing therapies. Agreements with pharmaceutical and biotechnology companies entered will include royalty rights on products derived from this data.

Importantly, the company may use the generated revenue to conduct biological research of its own that will provide potential for the development of commercial products.

IV. Business Flow

FIG. 1 illustrates overall steps in the business method herein. As shown, at step 101 initial genomic samples are obtained, such as from a clinical population available through a hospital or university. In most embodiments of the business method, the sample sources will include genomic DNA from human sources, although other organisms may be utilized as well. At step 110 the chromosomes are separated to form individual chromosomes. Such separation utilizes, in a preferred embodiment, somatic cell hybrid technology as described in U.S. Ser. No. 60/332,550, filed Nov. 26, 2001, entitled "Methods of Genomic Analysis" incorporated herein by reference for all purposes.

At step 120 the genomes are scanned for variants from a baseline sequence in a reference database 130. The reference database may be proprietary or a public database such as GenBank. Preferably, more than 10 different sources are scanned (it being understood that a single organism contains the genetic code from two different sources). In more preferred embodiments, more than 20 different sources are scanned, preferably more than 25 different sources, more preferably more than 30 different sources, preferably more than 50 different sources. As described in U.S. Pat. No. 6,897,025, the scanning step may be a one or two step process. In a two step process the each consecutive base in a genetic sequence is analyzed initially, and only those variants that are identified in the initial step are utilized for scanning in later grouping processes. The scanning step can utilize a number of technology platforms such as chips, capillary or gel based DNA sequencers, microtiter hybridization wells or others. The genomes that are scanned are preferably from genetically diverse groups such as different racial groups. This will assume that evolutionarily older, generally common SNPs are identified.

Preferably, the entire genetic code in the reference database analyzed or scanned for variants. Preferably, at least the non-repeat regions of the reference database are analyzed. Preferably, gene and non-gene regions of the sequences in the database are analyzed. Preferably, more than 1,000,000 bases are analyzed, preferably more than 10,000,000, more preferably more than 100,000,000, more preferably more than 500,000,000, and more preferably more than 1,000,000,000 bases. Preferably, more than 50% of at least one chromosome is scanned in multiple samples, preferably more than 2 chromosomes, preferably more than 5 chromosomes, and most preferably all of the chromosomes in the particular organism under study. By "common" SNPs, it is intended to refer to SNPs occurring in more than 2% of the sample population studied, preferably more than 4% of the population studied, preferably more than 6% of the population studied, preferably more than 8% of the population studied, and more preferably more than 10% of the population studied. Of course, rare SNPs can also be utilized in particular association studies at step 125 for commercialization of diagnostics and therapeutics and at step 135 as an adjunct to the other methods herein. Furthermore, the wafers used herein may also be used to compare genomes of, e.g. humans with other organisms such as mouse, rat or dog to, e.g. identify conserved regions as step 123.

The SNPs (and, potentially haplotype block and other information) are stored in a database 121, which may be, in whole or in part, licensed directly for revenue.

At step 140 the common variants are placed into haplotype blocks, in one case according to the methods in U.S. Ser. Nos. 60/280,530, filed Mar. 30, 2001; 60/313,264, filed Aug. 17, 2001; 60/327,006, filed Oct. 5, 2001; 60/332,550, filed Nov. 26, 2001; and U.S. Pat. No. 6,969,589, previously incorporated herein by reference. Representative variants and haplotype blocks from an entire human chromosome (chromosome 21) are disclosed in, for example, Patil, N. et al, "Blocks of Limited Haplotype Diversity Revealed by High-Resolution Scanning of Human Chromosome 21" *Science* 294, 1719–1723 (2001) and the associated supplemental materials, incorporated herein by reference. At step 142 representative informative SNPs are selected from among the haplotype blocks to be used in association studies.

The SNPs selected in step 142 may be used in a variety of applications. For example, in collaboration with other companies, one may select portions of the genome of the organism at step 144 that are believed to play a role in a particular phenotype such as a disease state. A partner may or may not provide the funding at step 146 and/or a sample set of, for example, diseased and control individuals with clinical information at step 148. At step 150 the representative SNPs are used in genotyping assay (such as a chip based assay, "Invader" assay (an enzyme-substrate reaction for quantifying DNA and RNA by binding two short DNA probes to a target, enzymatically cleaving the target, binding a fluorescently labeled probe to the cleavage site and the cutting the probe bound DNA to detect a fluorescence signal), "Taqman" assay (a fluorogenic probe-based assay available from Applied Biosystems (Foster City, Calif.), or gel or capillary sequencing operation) to determine which portions of the tentatively selected functional region do in fact correlate with the phenotype of interest. In this step, and other correlation studies described herein, more than 100 disease and control samples are preferably used (although they need not be from a common family group or genetically related pool of individuals, and are preferably selected to be from genetically diverse populations such as from different ethnic groups), preferably more than 200, more preferably more than 500, preferably more than 1000, and more preferably more than 200 disease and control samples.

The funding for use in the business methods herein will normally take on multiple forms. For example, the funding may be by way of funding for costs of performing the particular study in question, in some cases with margin. In addition funding may be provided by way of milestone payments, for example, at the time the SNPs/haplotypes are identified in the region, at the time the association study is completed, at the time clinical trials of various stages are started and/or completed, at the time drugs or diagnostics begin to be marketed and/or reach sales milestones, and/or royalties on sales of the relevant drug, diagnostic, or drug sold in conjunction with the population segregation diagnostic, or similar fees for other products such as agricultural products or consumer products. In addition, particular partners may provide funding by way of equity investment, and/or equity may be sold to investors.

Alternatively or in addition, at step 152 whole genome studies are performed in which the representative SNPs (selected in step 142 across all or a substantial part of the genome) are correlated with a phenotypic state such as a disease. This step may also be performed in collaboration with others, who may provide samples at step 154 and/or funding at step 156. Of course, the sample source and the funding source may or may not be the same in each of the studies herein. For example, the funding source may be a pharmaceutical company and the source of samples may be a hospital, academic research center, or another company.

A number of activities can be based upon the results of steps 150 and 152. For example, at step 158 diagnostic markers may be used to develop diagnostic tests that are indicative of a patient tendency to a disease (or, for example, being a carrier of a disease variant). Based on the markers, the diagnostics may be developed and commercialized at step 160. The diagnostics may take on a number of forms such as immunoassays, chip based DNA assays, PCR assays, Taqman assays, sequencing based assays, or the like.

In addition or instead, at step 162 the association studies are used to select disease targets for drug development. Once a genetic locus or multiple loci in the genome are associated with a particular phenotypic trait, for example, a disease susceptibility locus, the gene or genes or regulatory elements responsible for the trait can be identified. These genes or regulatory elements may then be used as therapeutic targets for the treatment of the disease, as shown in step 164 of FIG. 1 for commercialization at step 166, alone or in collaboration with partners. The genomic sequences identified by the methods of the present invention may be genic or nongenic sequences. The term identified "gene" is intended to mean the open reading frame encoding specific polypeptides, intronic regions, generally as well as adjacent 5' and 3' non-coding nucleotide sequences involved in the regulation of expression of the gene up to about 10 kb beyond the coding region, but possibly further in either direction. The coding sequences (ORFs) of an identified gene may affect the disease state due to their effect on protein structure. Alternatively, the noncoding sequences of the identified gene or nongenic sequences may affect the disease state by impacting the level of expression or specificity of expression of a protein. Genomic sequences are studied generally by isolating the identified gene substantially free of other nucleic acid sequences that do not include the genic sequence. The DNA sequences are used in a variety of ways. For example, the DNA may be used to detect or quantify expression of the gene in a biological specimen. The manner in which one probes cells for the presence of particular nucleotide sequences is well established in the literature and does not require elaboration here, see, e.g., Sambrook, et al., *Molecular Cloning: A Laboratory Manual* (Cold Spring Harbor Laboratory, New York) (1989).

Alternatively, individuals may be studied that are resistant to a particular disease, such as HIV. By understanding the genetic basis of disease resistance it may be possible to identify therapeutic and/or diagnostic targets.

According to one aspect of the invention, when a region of the genome has been identified as playing a role in a phenotypic state, this region of the genome may be the subject of further SNP scanning at step 120 to, for example, identify rare SNPs that may be associated with the disease. These SNPs may play a role in, for example, rare forms of the disease.

In addition, the sequence of the gene (including flanking promoter regions and coding regions) may be mutated in various ways known in the art to generate targeted changes in promoter strength, or changes in the sequence of the encoded protein, etc. The sequence changes may be substitutions, translocations, insertions or deletions. Deletions may further include larger changes, such as deletions of a domain or exon. Techniques for in vitro mutagenesis of cloned genes are known. Examples of protocols for site specific mutagenesis may be found in Gustin, et al., *Biotechniques* 14:22 (1993); Barany, *Gene* 37:111–23 (1985); Colicelli, et al., *Mol. Gen. Genet.* 199:537–9 (1985); Prentki, et al., *Gene* 29:303–13 (1984); Sambrook, et al., *Molecular Cloning: A Laboratory Manual* (Cold Spring Harbor Press) pp. 15.3–15.108 (1989); Weiner, et al., *Gene* 126:35–41 (1993); Sayers, et al., *Biotechniques* 13:592–6 (1992); Jones and Winistorfer, *Biotechniques* 12:528–30 (1992); and Barton, et al., *Nucleic Acids Res.* 18:7349–55 (1990). Such mutated genes may be used to study structure/function relationships of the protein product, or to alter the properties of the protein that affect its function or regulation.

The identified gene may be employed for producing all or portions of the resulting polypeptide. To express a protein product, an expression cassette incorporating the identified gene may be employed. The expression cassette or vector generally provides a transcriptional and translational initiation region, which may be inducible or constitutive, where the coding region is operably linked under the transcriptional control of the transcriptional initiation region, and a transcriptional and translational termination region. These control regions may be native to the identified gene, or may be derived from exogenous sources.

The peptide may be expressed in prokaryotes or eukaryotes in accordance with conventional methods, depending upon the purpose for expression. For large scale production of the protein, a unicellularorganism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In many situations, it may be desirable to express the gene in eukaryotic cells, where the gene will benefit from native folding and post-translational modifications. Small peptides also can be synthesized in the laboratory. With the availability of the protein or fragments thereof in large amounts, the protein may be isolated and purified in accordance with conventional ways. A lysate may be prepared of the expression host and the protein purified using HPLC, exclusion chromatography, gel electrophoresis, affinity chromatography, or other purification technique.

An expressed protein may be used for the production of antibodies, where short fragments induce the expression of antibodies specific for the particular polypeptide, and larger fragments or the entire protein allow for the production of antibodies over the surface of the polypeptide (polyclonal antibodies). Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes are immortalized by cell fusion and screened for high affinity antibody binding. The immortalized cells, i.e, hybridomas, producing the desired antibodies may then be expanded. For further description, see *Monoclonal Antibodies: A Laboratory Manual*, Harlow and Lane, eds. (Cold Spring Harbor Laboratories, Cold Spring Harbor, N.Y.) (1988). If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

The identified genes, gene fragments, or the encoded protein or protein fragments may be useful in gene therapy to treat degenerative and other disorders. For example, expression vectors may be used to introduce the identified gene (or variant thereof) into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to be transiently or stably maintained in the cells. The gene or protein product may be introduced into tissues or host cells by any number of routes, including viral infection, microinjection, or fusion of vesicles. Jet injection may also be used for intramuscular administration, as described by Furth, et al., *Anal. Biochem*, 205:365–68 (1992). Alternatively, the DNA may be coated onto gold microparticles, and delivered intradermally by a particle bombardment device, or "gene gun" as described in the literature (see, for example, Tang, et al., *Nature*, 356: 152–54 (1992)).

Antisense molecules can be used to down-regulate expression of the identified gene in cells. The antisense reagent may be antisense oligonucleotides, particularly synthetic antisense oligonucleotides having chemical modifications, or nucleic acid constructs that express such antisense molecules as RNA. The antisense sequence may be complementary to the mRNA of the targeted gene, and inhibits expression of the targeted gene products. Antisense molecules inhibit gene expression through various mechanisms, e.g., by reducing the amount of mRNA available for translation, through activation of RNAse H, or by steric hindrance. One or a combination of antisense molecules may be administered, where a combination may comprise multiple different sequences.

As an alternative to antisense inhibitors, catalytic nucleic acid compounds, e.g., ribozymes, anti-sense conjugates, etc., may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman, et al., *Nucl. Acids Res*. 23:4434–42 (1995)). Examples of oligonucleotides with catalytic activity are described in WO 9506764. Conjugates of antisense oligonucleotides with a metal complex, e.g. terpyridylCu(II), capable of mediating mRNA hydrolysis are described in Bashkin, et al., *Appl. Biochem. Biotechnol*. 54:43–56 (1995).

In addition to using the identified sequences for gene therapy, the identified nucleic acids can be used to generate genetically modified non-human animals to create animal models of diseases or to generate site-specific gene modifications in cell lines for the study of protein function or regulation. The term "transgenic" is intended to encompass genetically modified animals having an exogenous gene that is stably transmitted in the host cells where the gene may be altered in sequence to produce a modified protein, or having an exogenous promoter operably linked to a reporter gene. Transgenic animals may be made through homologous recombination, where the gene locus is altered. Alternatively, a nucleic acid construct is randomly integrated into the genome. Vectors for stable integration include plasmids, retroviruses and other animal viruses, YACs, and the like. Of interest are transgenic mammals, e.g., cows, pigs, goats, horses, etc., and, particularly, rodents, e.g., rats, mice, etc.

Investigation of genetic function may also utilize non-mammalian models, particularly using those organisms that are biologically and genetically well-characterized, such as *C. elegans, D. melanogaster* and *S. cerevisiae*. The subject gene sequences may be used to knock-out corresponding gene function or to complement defined genetic lesions in order to determine the physiological and biochemical pathways involved in protein function. Drug screening may be performed in combination with complementation or knock-out studies, e.g., to study progression of degenerative disease, to test therapies, or for drug discovery.

In addition, the modified cells or animals are useful in the study of protein function and regulation. For example, a series of small deletions and/or substitutions may be made in the identified gene to determine the role of different domains in enzymatic activity, cell transport or localization, etc. Specific constructs of interest include, but are not limited to, antisense constructs to block gene expression, expression of dominant negative genetic mutations, and over-expression of a the identified gene. One may also provide for expression of the identified gene or variants thereof in cells or tissues where it is not normally expressed or at abnormal times of development. In addition, by providing expression of a protein in cells in which it is otherwise not normally produced, one can induce changes in cellular behavior.

Protein molecules may be assayed to investigate structure/function parameters. For example, by providing for the production of large amounts of a protein product of an identified gene, one can identify ligands or substrates that bind to, modulate or mimic the action of that protein product. Drug screening identifies agents that provide, e.g., a replacement or enhancement for protein function in affected cells or for agents that modulate or negate protein function. The term "agent" as used herein describes any molecule, e.g. protein or small molecule, with the capability of altering or mimicking the physiological function of an identified gene or gene product. Generally a plurality of assays are run in parallel with different agent concentrations to obtain a differential response to the various concentrations. Typically, one of these concentrations serves as a negative control, i.e., at zero concentration or below the level of detection.

A wide variety of assays may be used for this purpose, including labeled in vitro protein-protein binding assays, protein-DNA binding assays, electrophoretic mobility shift assays, immunoassays for protein binding, and the like. Also, all or a fragment of the purified protein may also be used for determination of three-dimensional crystal structure, which can be used for modeling intermolecular interactions, membrane fusion, etc.

Candidate agents encompass numerous chemical classes, though typically they are organic molecules, preferably small organic compounds, having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, and frequently at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, benzodiazapines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc may be used.

Agents may be combined with a pharmaceutically acceptable carrier, which term includes any and all solvents, dispersion media, coatings, anti-oxidant, isotonic and absorption delaying agents and the like. The use of such media and agents for pharmaceutically active substances is well known in the art. Except insofar as any conventional media or agent is incompatible with the active ingredient, its use in the therapeutic compositions and methods described herein is contemplated. Supplementary active ingredients can also be incorporated into the compositions.

The formulation may be prepared for use in various methods for administration. The formulation may be given orally, by inhalation, or may be injected, e.g. intravascular, intratumor, subcutaneous, intraperitoneal, intramuscular, etc. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In some cases, oral administration will require a higher dose than if administered intravenously. Identified agents of the invention can be incorporated into a variety of formulations for therapeutic administration. More particularly, the complexes can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the agents can be achieved in various ways. Agents may be systemic after administration or may be localized by the use of an implant that acts to retain the active dose at the site of implantation.

For oral preparations, an agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Additionally, agents may be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Further, agents may be utilized in aerosol formulation to be administered via inhalation. The compounds of the present invention can be formulated into pressurized acceptable propellants such as dichlorodifluoromethane, propane, nitrogen and the like. Furthermore, agents may be made into suppositories by mixing with a variety of bases such as emulsifying bases or water-soluble bases. Alternatively, identified agents of the present invention can be administered rectally via a suppository. The suppository can include vehicles such as cocoa butter, carbowaxes and polyethylene glycols, which melt at body temperature, yet are solid at room temperature.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing identified agents of the present invention may be placed in proximity to the site of action, so that the local concentration of active agent is increased relative to the rest of the body. Unit dosage forms for oral or rectal administration such as syrups, elixirs, and suspensions may be provided wherein each dosage unit, for example, teaspoonful, tablespoonful, gel capsule, tablet or suppository, contains a predetermined amount of the compositions of the present invention. Similarly, unit dosage forms for injection or intravenous administration may comprise the compound of the present invention in a composition as a solution in sterile water, normal saline or another pharmaceutically acceptable carrier. The specifications for the novel unit dosage forms of the present invention depend on the particular compound employed and the effect to be achieved, and the pharmacodynamics associated with each active agent in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

A therapeutic dose of an identified agent is administered to a host suffering from a disease or disorder. Administration may be topical, localized or systemic, depending on the specific disease. The compounds are administered at an effective dosage that over a suitable period of time substantially arrests the disease progression. It is contemplated that the composition will be obtained and used under the guidance of a physician for in vivo use.

The dose will vary depending on the specific agent and formulation utilized, type of disorder, patient status, etc., at a dose sufficient to address the disease or symptoms thereof, while minimizing side effects. Treatment may be for short periods of time, e.g., after trauma, or for extended periods of time, e.g., in the prevention or treatment of schizophrenia.

In addition or in the alternative, at step 168 the phenotypic trait of drug response is used to stratify patients into various groups. The groups may be, for example, those that respond to a drug versus those that do not respond, those that respond to a drug without toxic effects, versus those that are observed to have toxic effects. At step 170 the therapeutic may be marketed with an associated diagnostic that is capable of segregating those that will respond an acceptable manner to the drug from those that do not.

According to one aspect of the invention herein, the technology platform used for one or both of the scanning steps 120 and/or the correlation step 150 or 152 is made available at a low or reduced price to the organization conducting the research into biology discussed herein, preferably exclusively for at least a period of time in a specified field. In return the technology provider receives from the business organization discussed herein one or more of equity, royalties on discoveries, licenses to the content generated in one or both of steps 120, 150, and 152 in a selected field and/or improvements to the technology platform, such as improvements made to chip technology. In an alternative embodiment, the organization conducting the research discussed herein is formed as a "tracking stock" of the technology provider. In preferred embodiments, the technology provider does not maintain control (as defined by the relevant accounting standard) of the organization performing the business methods elsewhere discussed herein. In this aspect of the invention, the early financial losses of the research organization need not be consolidated with the technology provider.

It is to be understood that the above description is intended to be illustrative and not restrictive. The scope of the invention should, therefore, be determined not with reference to the above description, but instead with reference to the appended claims along with the full scope of equivalents thereto.

What is claimed is:

1. The business method comprising:
   a. identifying genetic variations in a plurality of individuals comprising scanning more than 10,000,000 bases;
   b. identifying at least one of said genetic variations that is genetically linked with at least one other of said genetic variations; and
   c. collaborating with a partner to correlate said one of said genetic variations that is genetically linked with at least one other of said genetic variations with a phenotypic state.

2. The business method of claim 1, wherein said genetic variations are single nucleotide polymorphisms.

3. The business method of claim 1 wherein said genetic variations occur in more than 2% of said individuals.

4. The business method of claim 1 wherein said plurality of individuals is comprised of individuals from a set of different ethnic groups.

5. The business method of claim 1 wherein said phenotypic state is selected from the group consisting of adverse drug response, positive drug response, no drug response, ameliorated drug response in one patient as compared to another patient, and reduced drug response in one patient as compared to another patient.

6. The business method of claim 1 wherein said partner funds said collaboration step.

7. The business method of claim 1 further comprising the step of using results from the collaborating step to stratify patients.

8. The business method of claim 1 further comprising the step of using the results from the collaborating step to generate diagnostics.

* * * * *